(12) United States Patent
Chen

(10) Patent No.: US 7,544,279 B2
(45) Date of Patent: Jun. 9, 2009

(54) GEL CASTING MODULE AND ELECTRODE MODULE OF AN ELECTROPHORESIS DEVICE

(75) Inventor: Hui-Wan Chen, Taipei County (TW)

(73) Assignee: Wealtec Bioscience Co., Ltd. (TW)

( * ) Notice: Subject to any disclaimer, the term of this patent is extended or adjusted under 35 U.S.C. 154(b) by 961 days.

(21) Appl. No.: 11/150,157

(22) Filed: Jun. 13, 2005

(65) Prior Publication Data
US 2006/0278533 A1 Dec. 14, 2006

(51) Int. Cl.
*G01N 27/453* (2006.01)
*B29C 33/22* (2006.01)

(52) U.S. Cl. ........................ 204/620; 204/619; 204/616; 249/139

(58) Field of Classification Search ......... 204/616–620, 204/466, 467, 469, 470; 249/139
See application file for complete search history.

(56) References Cited

U.S. PATENT DOCUMENTS

2004/0195103 A1* 10/2004 Zhou .......................... 204/467

* cited by examiner

Primary Examiner—Alex Noguerola
(74) Attorney, Agent, or Firm—Bacon & Thomas, PLLC

(57) ABSTRACT

A gel casting module and an electrode module provided on a caster in an electrophoresis device having at least a recess provided for clinging thereto of a flat plate of a gel plate sandwich, a caster lid is provided on the lower side of the recess of the caster and can be turned to press on the recess; the caster is provided on two sides of its shoulder with clasps for fixing or releasing the caster lid, thereby the caster is used as a main-body for the gel casting module and the electrode module to position the gel plate sandwich. When in use, it needs only to do an action of closing the caster lid, the gel plate sandwich can be surely fixed on the caster; this not only increases the convenience of operation, but also largely simplifies the operation procedure for electrophoresis gel casting and running.

13 Claims, 6 Drawing Sheets

GEL CASTING MODULE AND ELECTRODE MODULE OF AN ELECTROPHORESIS DEVICE

BACKGROUND

1. Field of the Invention

The invention is related to modification of a gel casting module and an electrode module for electrophoresis applied to biological tests, and especially to offering a kind of simple and accurate gel casting module and an electrode module.

2. Description of the Prior Art

In biotech research field, the electrophoresis for separating/analysis of DNA, RNA and protein molecules, the advanced preparation procedures must have the two lateral sides and the bottoms of two mutually lapped flat plates tightly sealed, liquid gel solution is poured from an upper opening of a gap formed between the two flat plates, and a comb is placed in the opening, a gel plate sandwich containing the gel thus can be formed after gel is cured and solid gel is formed, then the comb is removed, and thus the pre-running gel forming procedure of the electrophoresis is completed.

After the gel forming procedure, the gel plate sandwich containing the two flat plates, spacers and the gel are correctly positioned in an electrophoresis tank, and then running buffer solution is poured in to the electrophoresis tank; after target samples to be separated/analyzed is loaded onto the gel on the gel plate sandwich, an electrode is connected to start the electrophoresis.

Thereby, in a practical electrophoresis device, a gel casting module must be used to fix and seal the surroundings of the flat plates and the spacers, and temporarily seal the bottom opening of the sandwich for gel solution loading and solidifying, and for shaping and smoothly completing fabrication of the gel plate sandwich. Further, before the gel plate sandwich is placed in the electrophoresis tank, it must be fixed on an electrode module, in order that it can be placed in the electrophoresis tank through the electrode module, and can be connected with the electrode module.

For example, U.S. Pat. Nos. 5,626,735 and 6,162,342 disclosed related structures of electrode modules for helping to press fix flat plates and spacers; wherein the U.S. Pat. No. 5,626,735 disclosed a conventional tool structure using screws to fix flat plates; such a tool must make the screws keep on rotating to reach a predetermined depth during using to surely press fix the flat plates, thereby it is relatively inconvenient for use, and the fabrication of the gel plate sandwich is slower.

While the U.S. Pat. No. 6,162,342 disclosed a gel casting module that takes advantage of bias moving of two rotary plates on two lateral sides thereof to press rearwards from the front on the two lateral sides of flat plates, and an upper inverse "T" shaped pressing plate is used to press down the flat plates; in practical using of such type of gel casting module, the rotary plates are not pressed rearwards from the front beneath the flat plates, thereby they has inferior capability of pressing on the flat plates, and the pressing function against the opening beneath the flat plates is also harder to be attained with clasps pushed by springs.

U.S. Pat. Nos. 5,632,877 and 6,110,340 disclosed structures of electrode modules for helping to fixedly connect a gel plate sandwich in an electrophoresis device; wherein the U.S. Pat. No. 5,632,877 disclosed an electrode module for putting a gel plate sandwich on a positioning caster, and then the positioning caster is placed in a fixing seat, the gel plate sandwich is fixed by rotating inwards of rotary plates on the two lateral sides of the fixing seat, at last, the gel plate sandwich, the positioning caster and the fixing seat are together put into a structures of an electrode module in an electrophoresis tank.

As to the U.S. Pat. No. 6,110,340, it disclosed an electrode module for which "U" shaped clamping members able to be pivoted inwards are provided on the two lateral sides of an electrophoresis device, and for which a sealing strip adapted to pivoting upwards are provided on the bottom of the device, when flat plates are placed in the electrophoresis device, after the clamping members pivot inwards to press on the gel plate sandwich, by engaging of two engaging hooks provided on the two lateral sides of the sealing strip into recesses of the clamping members, the gel plate sandwich is clamped tight.

However, although the above stated two conventional electrode modules for fixing and connecting a gel plate sandwich can get the object of fixing the gel plate sandwich, the modes of operation of tools used in fabrication of the gel plate sandwich are completely different; under the condition of using tools to fabricate the gel plate sandwich by different modes of operation, operation of the entire electrophoresis device becomes complicated and cumbersome, this is extremely subjected to influencing the accuracy of separating and analysis because of being not familiar with the methods of operation of related tools.

SUMMARY OF THE INVENTION

Accordingly, a caster for a gel casting module and an electrode module in an electrophoresis device of the present invention has at least a recess, the recess is provided for clinging thereto of a surface of a flat plate of a gel plate sandwich; a caster lid is provided on the lower side of the recess of the caster and can be turned upwards to press on the recess; the caster is provided on two sides of its shoulder with clasps for fixing or releasing the caster lid, thereby the caster is used as a main-body either for the gel casting module or the electrode module to position the gel plate sandwich.

Wherein the caster for the gel casting module has a pad on the side with the recess, the pad is made of elastic deformable material, and has a frame surrounding the bottom and the two lateral sides thereof, the frame of the pad is formed a structural portion that can correspondingly seal the edges of the bottoms and the lateral sides of two flat plates; the bottoms and the lateral sides of two flat plates can be elastically sealed by the edges of the frame of the pad to completely seat the frame of the frame of the pad and avoid liquid gel solution leakage just by pressing the clasps and covering the caster lid; and the two flat plates can be pressed on the caster, then the operation of gel loading can be completed by a simple mode of operation.

While the caster for the electrode module has an elastic rubber strip framing the recess, when the above-mentioned caster lid is pressed to cling to the recess, the elastic rubber strip is located between the gel plate sandwich and the recess to form a buffering and separation action to surely press fix the gel plate sandwich on the caster; thereby when the gel plate sandwich and the electrode module are placed subsequently into an electrophoresis tank and buffer solution is poured, an isolated buffer system can be formed (this is a conventional technique in performing electrophoresis, and no further narration is required) to avoid the danger of breaking of the gel plate sandwich by virtue of overly large pressure. Moreover, the electrode module is provided on the shoulder of the caster with related electrode connectors, so that after the gel plate sandwich and the electrode module are together placed in the electrophoresis tank, the buffer solution is poured, and a sample to be separated/analyzed is loaded onto the gel on the gel plate sandwich, an electrode is connected and the electrophoresis is started.

Particularly, the gel casting module and the electrode module of the present invention make fixing of the gel plate sandwich on the caster both by the mode of closing the caster lid and pressing the clasps, this not only can increase the convenience of operation, but also can largely simplify the method of operation of related tools for the electrophoresis device.

The present invention will be apparent in its combination and its mode of practicing after reading the detailed description of the preferred embodiment thereof in reference to the accompanying drawings.

DETAILED DESCRIPTION OF THE PREFERRED EMBODIMENT

Figure 1:
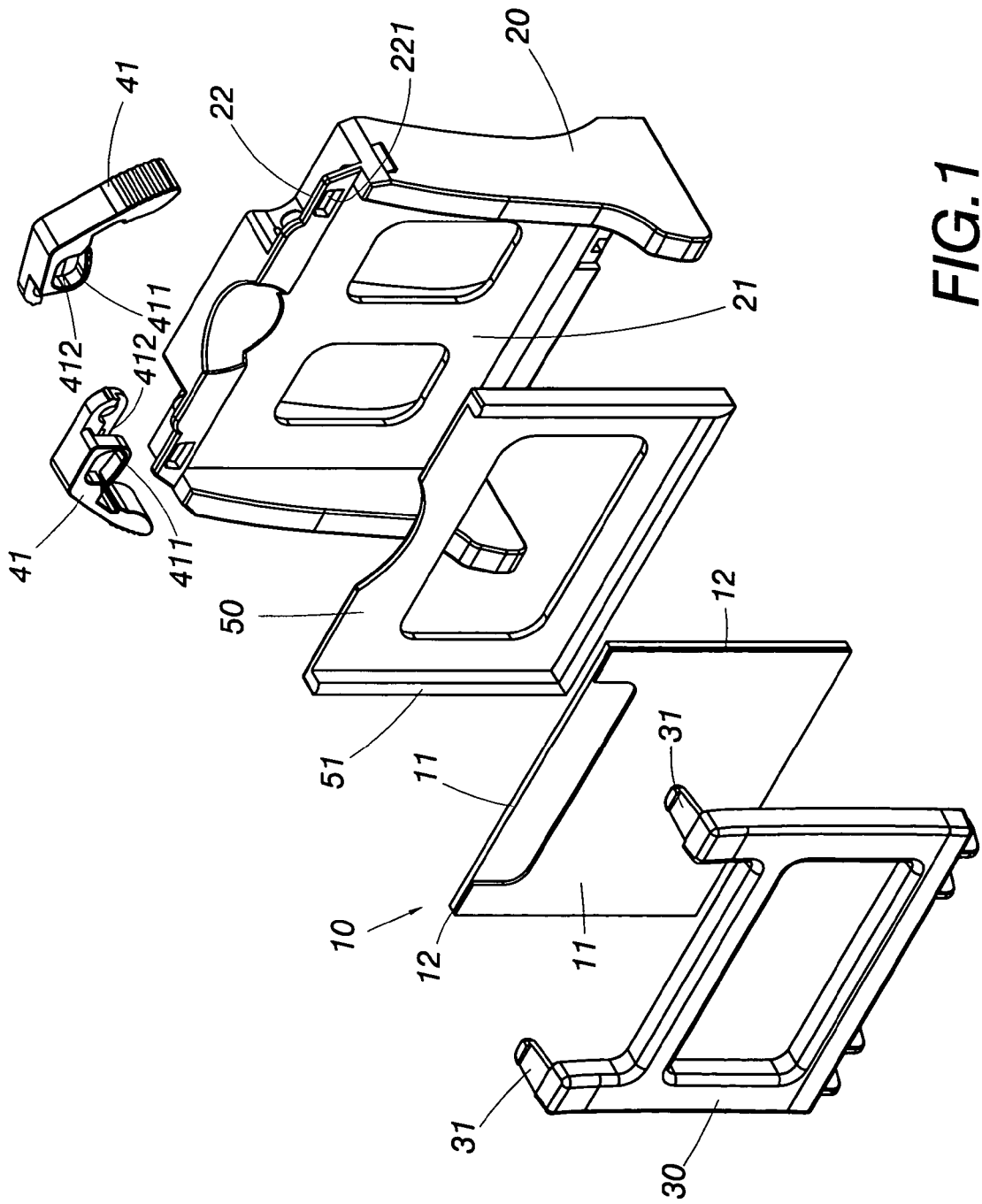
FIG. 1 is an anatomic perspective view showing the structure of a gel casting module of the present invention.
Figure 2:
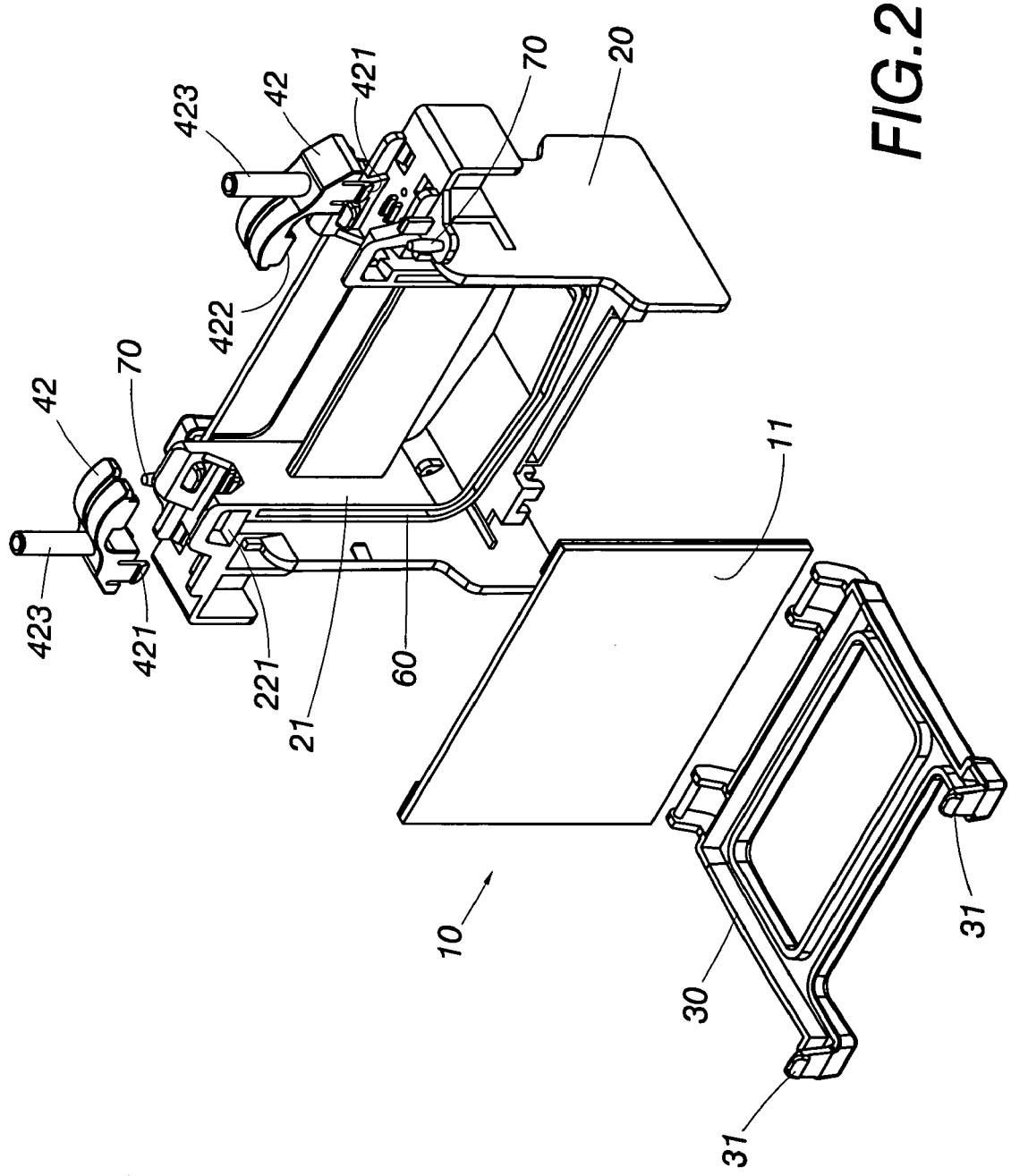
FIG. 2 is an anatomic perspective view showing the structure of an electrode module of the present invention.

The gel casting module and the electrode module in an electrophoresis device of the present invention are shown in FIGS. 1 and 2, in which the basic structures of the gel casting module and the electrode module both take a caster 20 as a main-body for positioning a gel plate sandwich 10; and in which the caster 20 either for the gel casting module shown in FIG. 1 or for the electrode module shown in FIG. 2 has at least a recess 21 for clinging thereto of a surface of a flat plate 11 of the gel plate sandwich 10.

A caster lid 30 is provided on the lower side of the recess 21 of the caster 20 and can be turned to press on the recess 21; the caster 20 is provided on two sides of its upper shoulder with clasps for fixing or releasing the caster lid 30. The clasps of the gel casting module and the electrode module shown in the drawings include first clasps 41 and second clasps 42 respectively.

As shown in FIG. 1, in particular practicing of the gel casting module, the caster 20 has a pad 50 on the side of the recess 21, the pad 50 has a frame 51 surrounding the bottom and the two lateral sides thereof, the frame 51 of the pad 50 is formed a structural portion that can correspondingly seal the edges of the lateral sides and the bottoms of two flat plates 11. In practicing, the pad 50 is preferably made of elastic deformable material such as rubber and silicone.

The lower edge of the abovementioned caster lid 30 is pivotally connected to the lower side of the recess 21 to render the caster lid 30 able to turn upwards; the upper edge of the caster lid 30 is provided transversely with hooks 31 able to engage with the first clasps 41. The two first clasps 41 of the gel casting module are pivotally provided on two sides of the shoulder of the caster 20, and can move bias downwards to a position able to engage with the hooks 31.

The caster 20 further is provided on its shoulder with a raised plate 22 which has holes 221 for extending therethrough of the hooks 31 of the caster lid 30 to engage with the first clasps 41.

Figure 3:
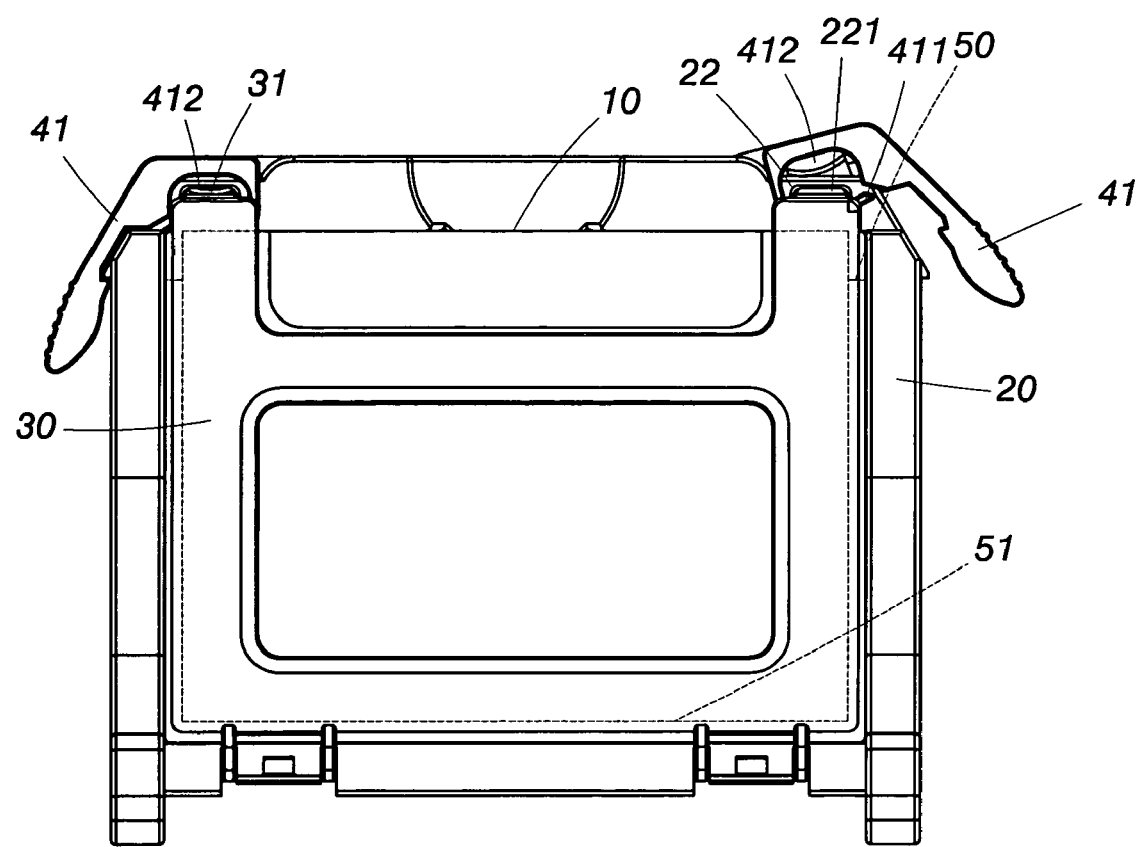
FIG. 3 is a schematic view showing the engaging state of clasps of the gel casting module with a caster lid of the present invention.
Figure 4:
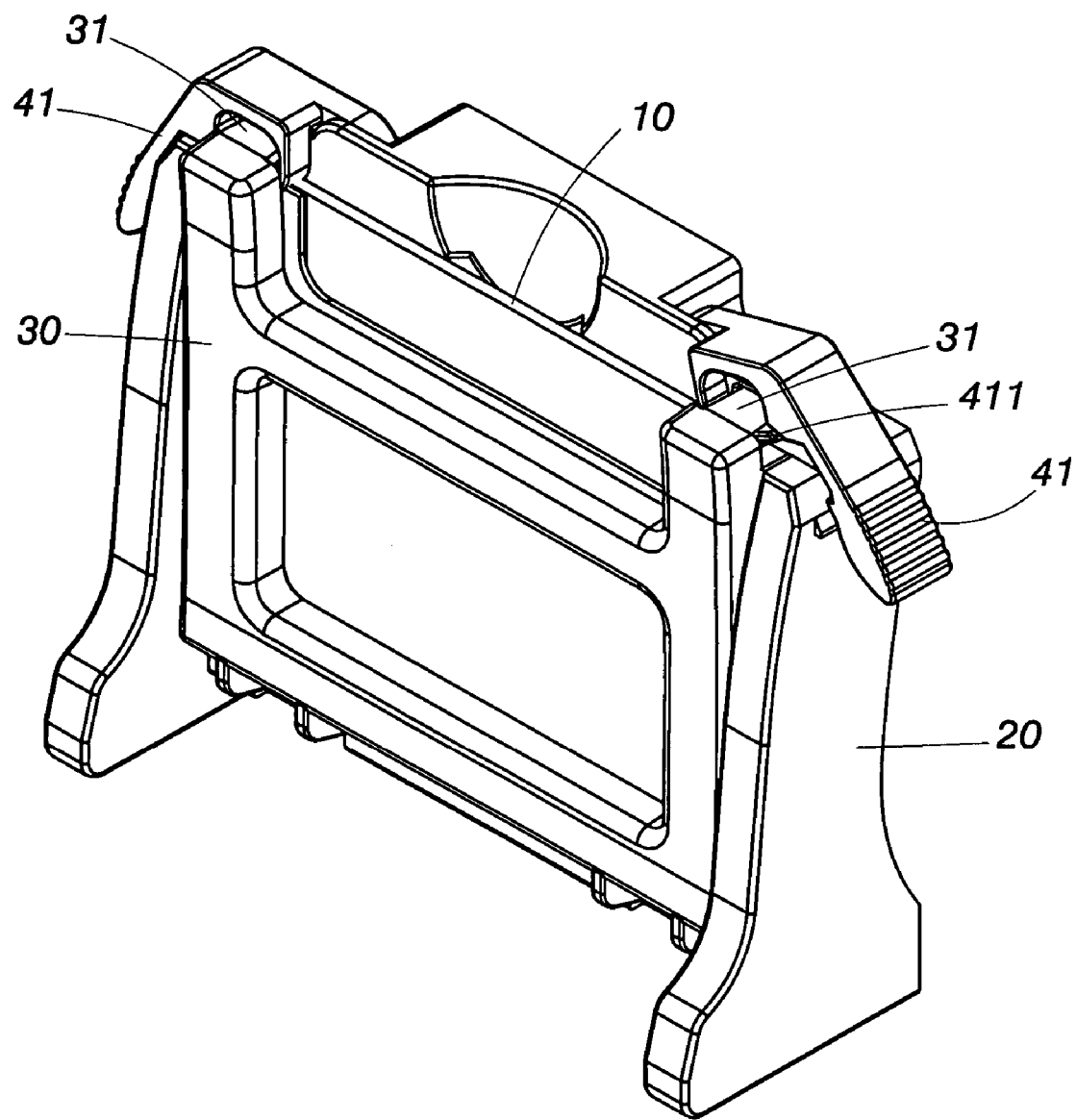
FIG. 4 is a schematic perspective view showing the folded state of the clasps of the gel casting module of the present invention.

Referring simultaneously to FIGS. 3, 4, the first clasps 41 of the gel casting module are further provided therebeneath each with a spring leaf 411 that is exactly beneath the raised plate 22, thereby the spring leaves 411 give a pressing force toward the bottom frame 51 of the pad 50; and the first clasps 41 are provided each with a stop piece 412, in order that the stop piece 412 is engaged with a hook 31 of the caster lid 30.

Therefore, it can be as shown in FIG. 1 that after the flat plates 11 of the gel plate sandwich 10 and two spacers 12 are placed in the recess 21 of the caster 20 to cling to the pad 50, the first clasps 41 of the gel casting module bias move downwards, so that the spring leaves 411 of the first clasps 41 press the flat plates 11 toward and against the bottom frame 51 of the pad 50 (as shown in FIG. 3), and the stop pieces 412 of the first clasps 41 are displaced to a position able to engage with the hooks 31.

At this time, the caster lid 30 moves toward the recess 21 for covering and positioning, after the hooks 31 of the caster lid 30 are extended through the holes 221 and engaged with the first clasps 41, the caster lid 30 can press the two flat plates 11 of the gel plate sandwich 10 toward and against the pad 50 and the recess 21 to complete the operation of positioning the flat plates 11.

In other words, after the two flat plates 11 and the two spacers 12 are placed in the pad 50 in the recess 21, just by the action of pressing the first clasps 41 and the caster lid 30, the bottoms of the two flat plates 11 can be surely pressed against the bottom frame 51 of the pad 50 and the two flat plates 11 can be surely pressed against the caster 20, while the lateral sides of two flat plates 11 can be surely pressed against the two spacers 12. Additionally, when the flat plates 11 are pressed against the caster 20, by having elasticity of the frame 51 of the pad 50, the edges on the bottoms and the lateral sides of the two flat plates 11 are tightly sealed, so that when in pouring liquid gel, an effect of preventing leakage can be obtained.

And after shaping of the gel, it needs only to fold the first clasps 41 of the gel casting module upwards (in a contrary direction) to release the stop pieces 412 from engaging with the hooks 31, the caster lid 30 can be opened to allow the gel plate sandwich 10 to be removed from the caster 20.

Figure 5:
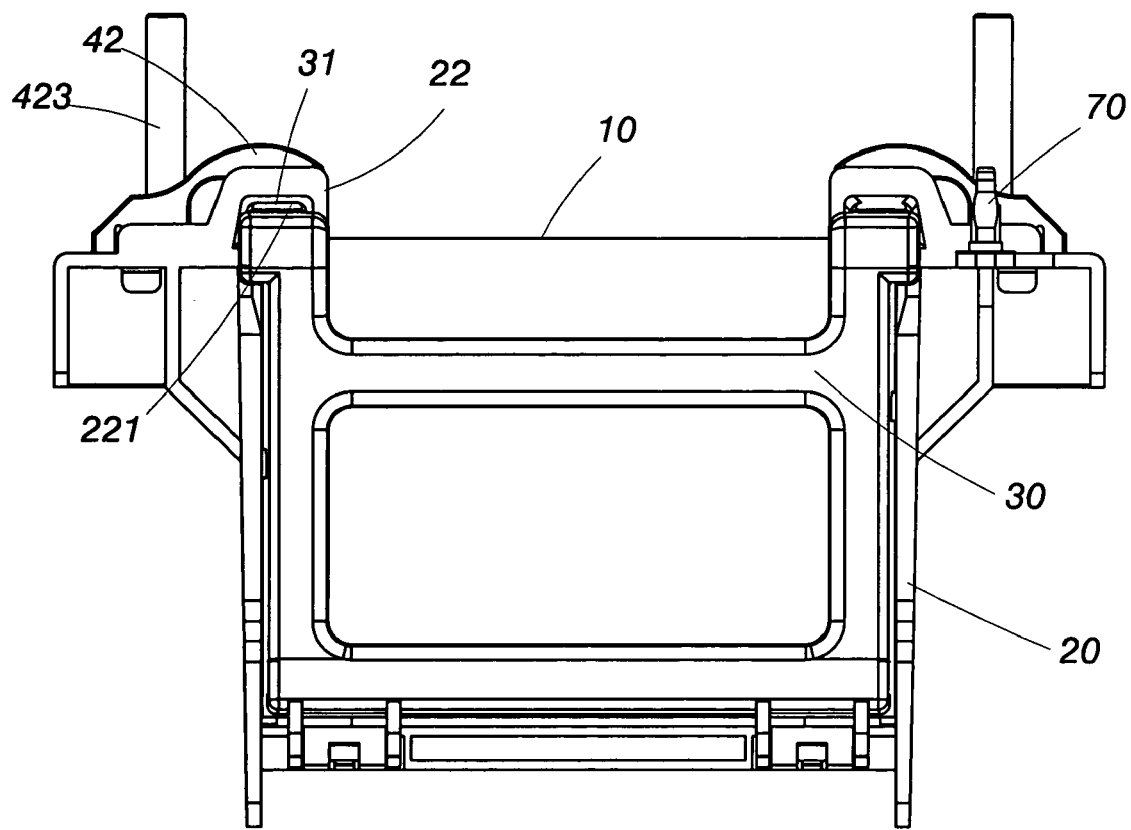
FIG. 5 is a schematic view showing the engaging state of the clasps of the electrode module with a caster of the present invention.

As shown in FIGS. 2 and 5, when the present invention is applied on the electrode module, the caster 20 has an elastic rubber or silicone strip 60 framing the recess 21 of the caster 20, and the caster 20 is provided on its shoulder with electrode connectors 70.

In practicing, the lower edge of the abovementioned caster lid 30 is pivotally connected to the lower side of the recess 21; the upper edge of the caster lid 30 is provided transversely with hooks 31 able to extend into the second clasps 42.

The second clasps 42 of the electrode module are engaged and fixed on the two sides of the shoulder of the caster 20 directly taking advantage of elastic hooking sheets 421, the tailing ends of the second clasps 42 have pressing portions 422 capable of pressing the hooks 31 down; and the caster 20 for the electrode module is provided on its shoulder with holes 221 for extending therethrough and engaging of the hooks 31, so that the hooks 31 of the caster lid 30 form engagement with the caster 20; and when the pressing portions 422 of the second clasps 42 press the hooks 31 down, the engagement of the hooks 31 with the caster 20 can be released.

Figure 6:
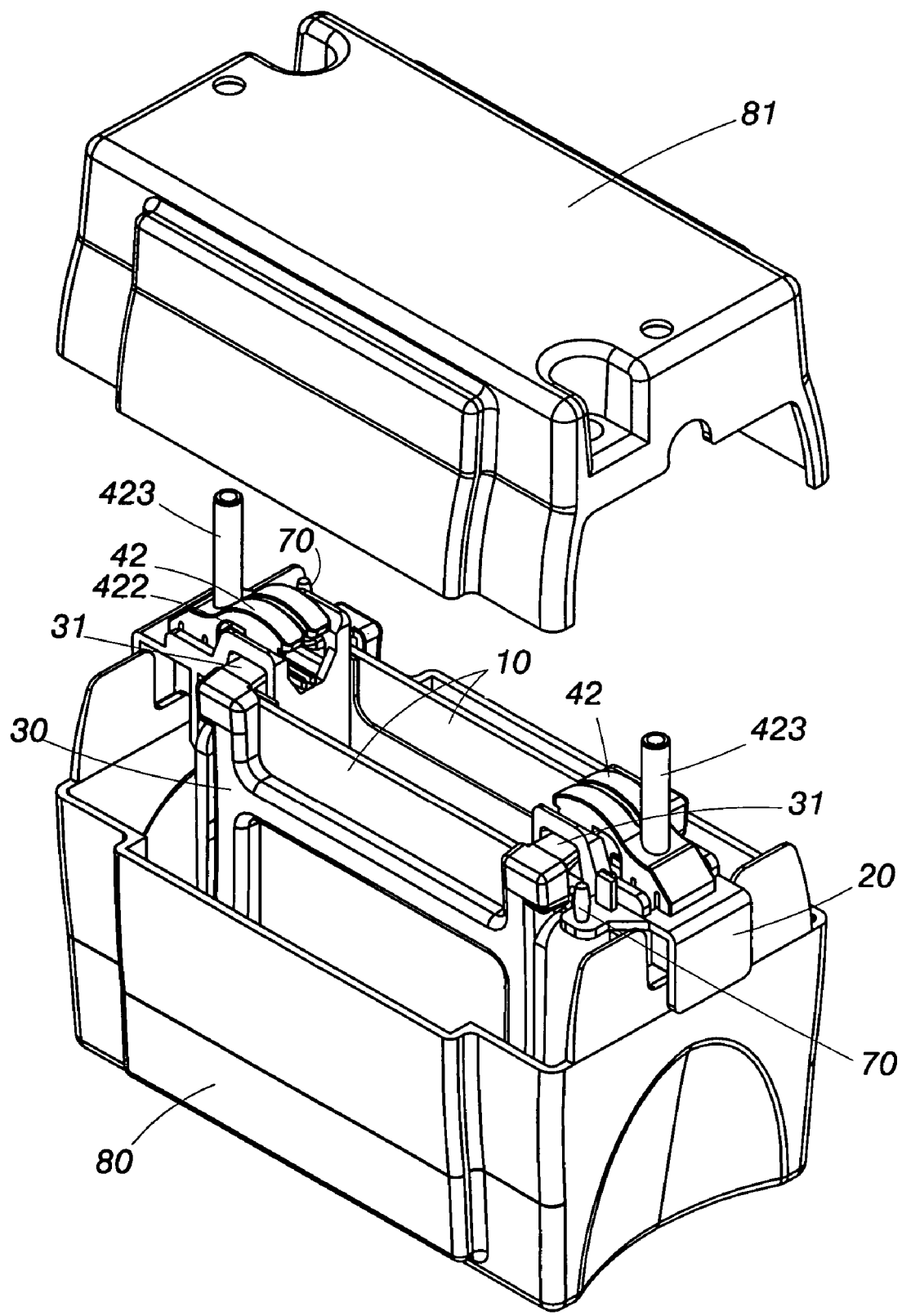
FIG. 6 is a schematic perspective view showing the state that the electrode module is placed in an electrophoresis tank of the present invention.

In this way, it needs only to do an action of closing the caster lid 30, and the gel plate sandwich 10 can be surely pressed on the recess 21 of the caster 20; and in pressing on, the strip 60 is located between the gel plate sandwich 10 and the recess 21 to form a buffering action; this can avoid the danger of breaking the gel plate sandwich 10 by an overly large pressure, thereby when the gel plate sandwich 10 and the electrode module are placed subsequently into an electrophoresis tank 80 (as shown in FIG. 6) and buffer solution is poured, an isolated buffer system can be formed (this is a conventional technique in performing electrophoresis, and no further narration is required). In subsequent using, it needs only to place the caster 20 of the electrode module together with the gel plate sandwich 10 into the electrophoresis tank 80, and to pour the buffer solution into the electrophoresis tank 80, and after the gel on the gel plate sandwich 10 is loaded thereon with a sample to be separated/analyzed, the electrode connectors 70 are connected to electrodes (not shown), and the electrophoresis can thus be started Particularly, the gel casting module and the electrode module of the present invention make fixing of the gel plate sandwich 10 on the caster 20 both by the mode of closing the caster lid; this not only can increase the convenience of operation, but also can largely simplify the method of operation of related tools for the electrophoresis device.

Moreover, in this embodiment, the second clasps 42 of the electrode module are provided with posts 423 able to extend out of an upper cover 81 of the electrophoresis tank 80, so that during the process of opening the upper cover 81 after completion of the electrophoresis, by pressing and hold the posts 423 simultaneously with fingers, the caster 20 of the electrode module is pressed toward a direction in contrary with that of upwardly opening the upper cover 81, the upper cover 81 can be smoothly opened and can avoid making shaking and scattering of the gel plate sandwich 10.

Accordingly, the present invention provides a gel casting module and an electrode module applied in an electrophoresis device to simplify the methods of operation of tools relating to the electrophoresis device. The embodiments given and shown in the drawings are only for illustrating the present invention, and not for giving any limitation to the scope of the present invention; it will be apparent to those skilled in this art that various equivalent modifications or changes without departing from the spirit of this invention shall also fall within the scope of the appended claims.

The invention claimed is:

1. A gel casting module for an electrophoresis device comprising: a caster having at least a recess for clinging thereto of a surface of a flat plate of a gel plate sandwich; a caster lid provided on a lower side of said recess of said caster and adapted to being pivoted to press on said recess; clasps for fixing said caster lid being provided on two sides of an upper shoulder of said caster; a pad provided on a side of said caster having said recess, and a frame at least provided on the bottom of said pad.

2. The gel casting module for an electrophoresis device as claimed in claim 1, wherein an upper edge of said caster lid is provided correspondingly with hooks adapted to engaging with said clasps; said clasps are provided each with a stop piece on one of said two sides of said upper shoulder of said caster, and are adapted to moving bias downwards to make said stop pieces move to positions for engaging with said hooks.

3. The gel casting module for an electrophoresis device as claimed in claim 2, wherein said caster further is provided on said shoulder with a raised plate which has holes for extending therethrough of said hooks.

4. The gel casting module for an electrophoresis device as claimed in claim 3, wherein said clasps are further provided each with a spring leaf that gives a force to press said gel plate sandwich toward and on said bottom frame of said pad.

5. The gel casting module for an electrophoresis device as claimed in claim 1, wherein a lower edge of said caster lid is pivotally connected to a lower side of said recess.

6. The gel casting module for an electrophoresis device as claimed in claim 1, wherein said pad is made of elastic deformable material, and has a frame surrounding a bottom and two lateral sides thereof.

7. An electrode module for an electrophoresis device comprising: a caster having at least a recess for clinging thereto of a surface of a flat plate of a gel plate sandwich; electrode connectors provided on two sides of a shoulder of said caster; a caster lid provided on a lower side of said recess of said caster and adapted to being pivoted to press on said recess, clasps for releasing said caster lid being provided on two sides of an upper shoulder of said caster; a rubber strip provided on said recess for clinging of said gel plate sandwich to said recess.

8. The electrode module for an electrophoresis device as claimed in claim 7, wherein an upper edge of said caster lid is provided correspondingly with hooks adapted to extending into said clasps; said caster is provided on said shoulder with holes for extending therethrough and engaging of said hooks.

9. The electrode module for an electrophoresis device as claimed in claim 8, wherein said two clasps are engaged and fixed on said two sides of said shoulder of said caster by using elastic hooking sheets.

10. The electrode module for an electrophoresis device as claimed in claim 7, wherein said two sides of said shoulder of said caster are provided with posts adapted to extending out of an upper cover of an electrophoresis tank.

11. The electrode module for an electrophoresis device as claimed in claim 7, wherein said two clasps are provided with posts adapted to extending out of an upper cover of an electrophoresis tank.

12. The electrode module for an electrophoresis device as claimed in claim 7, wherein a lower edge of said caster lid is pivotally connected to a lower side of said recess.

13. The electrode module for an electrophoresis device as claimed in claim 7, wherein said rubber strip is made of elastic material.

\* \* \* \* \*